(12) United States Patent
Ito et al.

(10) Patent No.: US 9,696,202 B2
(45) Date of Patent: Jul. 4, 2017

(54) METHOD FOR MAKING SURFACE ENHANCED RAMAN SCATTERING DEVICE

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Takashi Kasahara, Hamamatsu (JP); Yoshihiro Maruyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/971,049

(22) Filed: Dec. 16, 2015

(65) Prior Publication Data
US 2016/0109291 A1 Apr. 21, 2016

Related U.S. Application Data

(63) Continuation of application No. 13/962,583, filed on Aug. 8, 2013, now Pat. No. 9,267,894.

(30) Foreign Application Priority Data

Aug. 10, 2012 (JP) ................................ 2012-178976

(51) Int. Cl.
*H05K 3/02* (2006.01)
*H05K 3/10* (2006.01)
(Continued)

(52) U.S. Cl.
CPC ........... *G01J 3/0205* (2013.01); *G01J 3/4412* (2013.01); *G01N 21/658* (2013.01); *Y10T 29/49155* (2015.01)

(58) Field of Classification Search
CPC ...... G01N 21/658; G01N 21/65; B82Y 40/00; G01J 3/44; Y10T 29/49155; G02B 5/008; G02F 2203/10
(Continued)

(56) References Cited

U.S. PATENT DOCUMENTS 5,772,905 A * 6/1998 Chou .................... B29C 59/022
216/44
7,236,242 B2 * 6/2007 Kamins ................ G01N 21/658
356/301
(Continued)

FOREIGN PATENT DOCUMENTS

CN 101281133 10/2008
CN 101319994 12/2008
(Continued)

OTHER PUBLICATIONS

U.S. Office Action dated Oct. 14, 2016 that issued in U.S. Appl. No. 14/420,510 including Double Patenting Rejections on pp. 2-14.
(Continued)

*Primary Examiner* — Thiem Phan
(74) *Attorney, Agent, or Firm* — Drinker Biddle & Reath LLP

(57) ABSTRACT

A method for making a surface enhanced Raman scattering device in accordance with one aspect of the present invention comprises a first step of forming a nanoimprint layer on a main surface of a wafer including a plurality of portions each corresponding to a substrate; a second step of transferring, by using a mold having a pattern corresponding to a fine structural part, the pattern to the nanoimprint layer after the first step, and thereby forming the formed layer including the fine structural part for each portion corresponding to the substrate; a third step of forming a conductor layer on the fine structural part after the second step; and a
(Continued)

fourth step of cutting the wafer into each portion corresponding to the substrate after the second step.

5 Claims, 13 Drawing Sheets

Related U.S. Application Data

(60) Provisional application No. 61/682,406, filed on Aug. 13, 2012.

(51) Int. Cl.
*G01J 3/02* (2006.01)
*G01N 21/65* (2006.01)
*G01J 3/44* (2006.01)

(58) Field of Classification Search
USPC .............. 29/846, 825, 829, 849; 356/301
See application file for complete search history.

(56) References Cited

U.S. PATENT DOCUMENTS

| | | | |
|---|---|---|---|
| 7,460,224 | B2 | 12/2008 | Wang et al. |
| 7,483,130 | B2 | 1/2009 | Baumberg et al. |
| 7,864,313 | B2 | 1/2011 | Baumberg et al. |
| 8,416,406 | B2 | 4/2013 | Stuke et al. |
| 2004/0023046 | A1 | 2/2004 | Schlottig et al. |
| 2006/0146323 | A1 | 7/2006 | Bratkovski et al. |
| 2008/0094621 | A1 | 4/2008 | Li et al. |
| 2008/0218761 | A1 | 9/2008 | Nishikawa et al. |
| 2010/0195106 | A1 | 8/2010 | Ogawa |
| 2011/0027901 | A1 | 2/2011 | Gaster et al. |
| 2011/0116089 | A1 | 5/2011 | Schmidt et al. |
| 2011/0166045 | A1 | 7/2011 | Dhawan et al. |
| 2011/0300691 | A1 | 12/2011 | Sakamoto et al. |
| 2014/0043605 | A1 | 2/2014 | Tseng et al. |

FOREIGN PATENT DOCUMENTS

| | | |
|---|---|---|
| CN | 101400976 | 4/2009 |
| CN | 102282094 | 12/2011 |
| CN | 102307699 | 1/2012 |
| CN | 102483354 | 5/2012 |
| EP | 2469598 | 6/2012 |
| JP | 5-44867 | 6/1993 |
| JP | H07-260646 A | 10/1995 |
| JP | 2003026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008268059 A | 11/2008 |
| JP | 2009-025316 A | 2/2009 |
| JP | 2009047623 A | 3/2009 |
| JP | 2009103643 A | 5/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-215021 A | 10/2011 |
| JP | 2012233707 A | 11/2012 |
| WO | WO-2007/149120 A2 | 12/2007 |
| WO | WO-2008/013683 A2 | 1/2008 |
| WO | WO 2010/033267 | 3/2010 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO-2012/024006 A2 | 2/2012 |
| WO | WO 2013/015810 | 1/2013 |
| WO | WO 2013/058739 | 4/2013 |
| WO | WO-2014-025034 A1 | 2/2014 |
| WO | WO-2014/025034 A1 | 2/2014 |

OTHER PUBLICATIONS

English Machine Translation of JP 2011-107032, Nishikawa et al., Jun. 2, 2011 as attached to U.S. Office Action dated Oct. 14, 2016 in U.S. Appl. No. 14/420,510.

W. Zhang et al., "Giant and uniform fluorescence enhancement over large areas using plamonic nanodots in 3D resonant cavity nanoantenna by nanoimprinting", Nanotechnolgy, vol. 23, No. 22, May 10, 2012, p. 225301, XP020224099.

S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.

W. Wu et al., "Rational engineering of highly sensitive SERS substrate based on nanocone structures", Proceedings of SPIE, vol. 7673, Apr. 23, 2010, p. 767300-p. 767300-6, XP055172245.

L. Gang et al., "Nanowell surface enhanced Raman scattering arrays fabricated by soft-lithography for label-free biomolecular detections in integrated microfluidics", Applied Physics Letters, vol. 87, No. 7, Aug. 11, 2005, p. 74101, XP012077510.

K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.

M. Tomohiko et al., "New localized surface plasmon resonance sensor utilizing nanoimprinting technology", NSTI Nanotechnology Conference and Trade Show-NST1 Nanotech, vol. 1, May 11, 2006, p. 58-p. 61, XP009098538.

W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

Q-SERS™ G1 Substrate, Nanova Inc.

Masahiro Yanagisawa, "Detection of Trace Organic Gas Using Molecular Sensor with Plasmon Antenna," Green Techology, vol. 22, No. 6, Jun. 10, 2012, pp. 42-47, with English Translation.

Zhigiang Sun et al, "Fabricating Ordered Microstructures on the Basis of Self-assembled Colloidal Crystals", Major: Polymer Chemistry and Physics, vol. 8, Aug. 15, 2009, p. B014-p. 158.

\* cited by examiner

50nm

Fig.5
(a)
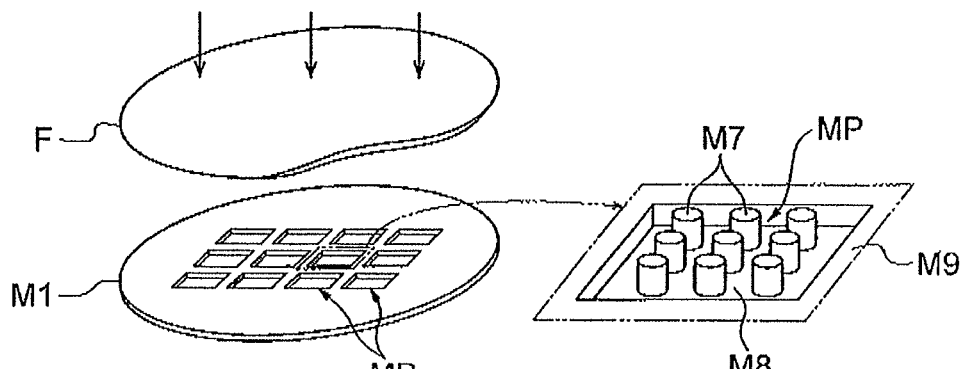
(b)
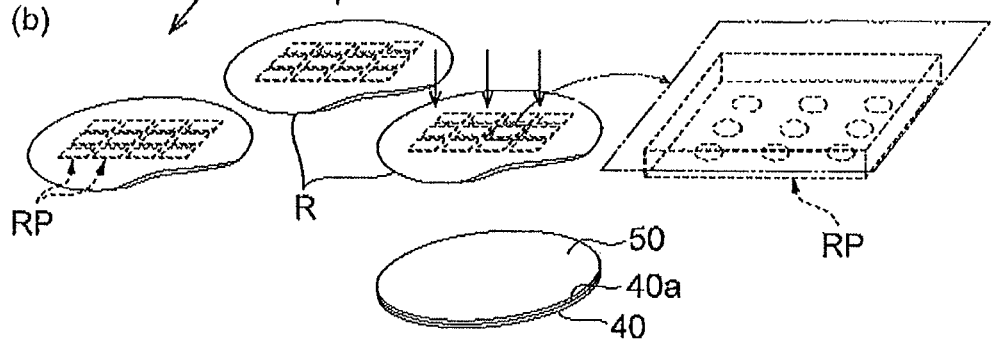
(c)
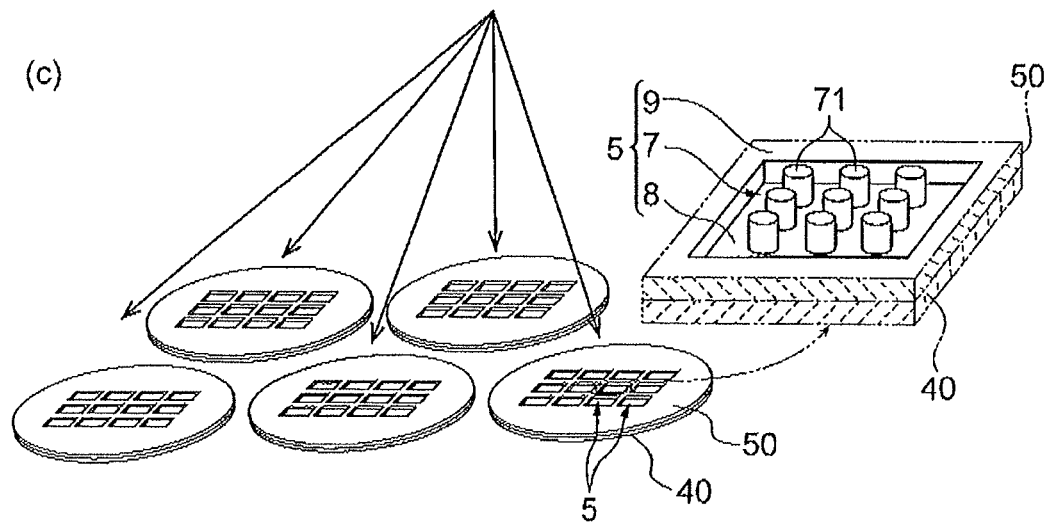

METHOD FOR MAKING SURFACE ENHANCED RAMAN SCATTERING DEVICE

CROSS-REFERENCE TO RELATED APPLICATIONS

This is a continuation application of copending prior application Ser. No. 13/962,583, filed on Aug. 8, 2013, which is incorporated by reference herein in its entirety.

This application claims priority to Provisional Application No. 61/682406 filed on Aug. 13, 2012, and Japanese Patent Application No. JP2012-178976 filed on Aug. 10, 2012, by the same applicant, which are hereby incorporated by reference in its entirety.

BACKGROUND OF THE INVENTION

Field of the Invention

The present invention relates to a method for making a surface enhanced Raman scattering device.

Related Background Art

As a conventional surface enhanced Raman scattering device, one comprising a fine metal structural part which generates surface enhanced Raman scattering (SERS) has been known (see, for example, Japanese Patent Application Laid-Open No. 2011-33518 and "Q-SERSTM G1 Substrate", [online], Opto Science, Inc., [retrieved on 2012-07-19], retrieved from the Internet <URL: http://www.optoscience.com/maker/nanova/pdf/Q-SERS_G1. pdf >). In such a surface enhanced Raman scattering device, a sample subjected to Raman spectrometry is brought into contact with the fine metal structural part. When the sample is irradiated with excitation light in this state, surface enhanced Raman scattering occurs, whereby Raman scattered light enhanced by about $10^8$ times, for example, is emitted.

As a method for making a surface enhanced Raman scattering device such as the one mentioned above, Japanese Patent Application Laid-Open No. 2011-75348, for example, describes a method comprising forming a plurality of fine pillars on a substrate by vapor deposition and further forming metal films at top parts of the pillars by vapor deposition, thereby producing a fine metal structural part.

SUMMARY OF THE INVENTION

However, the above-mentioned surface enhanced Raman scattering device making method forms a plurality of fine pillars on a substrate by vapor deposition and thus increases the time required for forming the pillars, while the pillars may have unstable forms.

It is therefore an object of the present invention to provide a surface enhanced Raman scattering device making method which can make a surface enhanced Raman scattering device efficiently and stably.

The surface enhanced Raman scattering device making method in accordance with one aspect of the present invention is a method for making a surface enhanced Raman scattering device comprising a substrate having a main surface; a formed layer formed on the main surface and including a fine structural part; and a conductor layer formed on the fine structural part and constituting an optical function part for generating surface enhanced Raman scattering; the method comprising a first step of forming a nanoimprint layer on a main surface of a wafer including a plurality of portions each corresponding to the substrate; a second step of transferring, by using a mold having a pattern corresponding to the fine structural part, the pattern to the nanoimprint layer after the first step, and thereby forming the formed layer including the fine structural part for each portion corresponding to the substrate; a third step of forming the conductor layer on the fine structural part after the second step; and a fourth step of cutting the wafer into each portion corresponding to the substrate after the second step.

This surface enhanced Raman scattering device making method transfers a pattern of a mold to a nanoimprint layer on a wafer, and thereby form a formed layer including a fine structural part for each portion corresponding to a substrate. This can form the fine structural part efficiently and stably. Therefore, this surface enhanced Raman scattering device making method can make a surface enhanced Raman scattering device efficiently and stably.

In the surface enhanced Raman scattering device making method in accordance with one aspect of the present invention, the fourth step may be performed after the third step. This can form a conductor layer collectively for a plurality of fine structural parts on the wafer, whereby the surface enhanced Raman scattering device can be made more efficiently.

In the surface enhanced Raman scattering device making method in accordance with one aspect of the present invention, the mold may be flexible. This makes it easier to release the mold from the nanoimprint layer. When a relatively large distortion or the like exists in the wafer in this case, the mold follows the distortion or the like in the wafer, whereby the fine structural part can be formed stably.

In the surface enhanced Raman scattering device making method in accordance with one aspect of the present invention, the mold may be elastic. In this case, foreign matters and the like, if any, intervening between the mold and the nanoimprint layer are likely to bite onto the mold. Therefore, areas of transfer failures can be suppressed. This can also make it easier for the pattern of the mold to follow the nanoimprint layer, and thereby form the fine structural part stably. Further, when relatively small roughness and the like exist in the wafer in this case, the mold follows the roughness and the like of the wafer, whereby the fine structural part can be formed more stably.

In the surface enhanced Raman scattering device making method in accordance with one aspect of the present invention, the mold may have a plurality of patterns, and in the second step, a plurality of the patterns may be simultaneously transferred to the nanoimprint layer by using the mold. This can collectively form a plurality of fine structural parts for the nanoimprint layer on the wafer, whereby the surface enhanced Raman scattering device can be made more efficiently.

In the surface enhanced Raman scattering device making method in accordance with one aspect of the present invention, a plurality of the patterns may be separated from each other, and in the second step, a plurality of the patterns may be simultaneously transferred to the nanoimprint layer by using the mold such that a plurality of fine structural parts are separated from each other. In this case, the wafer can be cut easily with reference to a space between adjacent fine structural parts as a guide for cutting.

In the surface enhanced Raman scattering device making method in accordance with one aspect of the present invention, a plurality of the patterns may be continuous, and in the second step, a plurality of the patterns may be simultaneously transferred to the nanoimprint layer by using the mold such that a plurality of fine structural parts are continuous. This can form a greater number of fine structural parts in a small area than in the case where a plurality of fine structural parts are formed so as to be separated from each other, whereby a greater number of surface enhanced Raman scattering devices can be obtained from the wafer.

In the surface enhanced Raman scattering device making method in accordance with one aspect of the present invention, in the fourth step, the formed layer and conductor layer existing on a line to cut passing between the portions corresponding to the substrates may be cut together with the wafer. This can integrally form the formed layer and conductor layer all over the portions corresponding to the substrates, whereby the surface enhanced Raman scattering devices can be made more efficiently.

In the surface enhanced Raman scattering device making method in accordance with one aspect of the present invention, in the fourth step, a fracture may be extended from a cutting start point formed in the wafer along the line and thereby the formed layer and conductor layer existing on the line are cut together with the wafer. This makes it unnecessary for the formed layer and conductive layer to be formed with a cutting start point and thus can inhibit the fine structural part and optical function part from being damaged.

In the surface enhanced Raman scattering device making method in accordance with one aspect of the present invention, the formed layer may include a support for supporting the fine structural part on the main surface of the substrate and a ring-shaped frame surrounding the support on the main surface of the substrate, and in the fourth step, a fracture may be extended from a cutting start point formed in the wafer along a line to cut passing between the portions corresponding to the substrates, and thereby the frame and conductor layer existing on the line are cut together with the wafer. In this case, the frame can favorably buffer shocks caused by cutting and the like, whereby the fine structural part and optical function part can be inhibited from being damaged at the time of cutting.

In the surface enhanced Raman scattering device making method in accordance with one aspect of the present invention, in the fourth step, the wafer may be irradiated with laser light while locating a converging point within the wafer, and thereby a modified region is formed as the cutting start point within the wafer along the line. In this case, the wafer is hardly affected by the irradiation with the laser light except for the vicinity of the converging point of the laser light therewithin, whereby the fine structural part and optical function part can be inhibited from being damaged at the time of cutting. Utilizing a fracture having extended from the modified region, the formed layer and conductor layer on the line can accurately be cut together with the wafer.

The present invention can provide a surface enhanced Raman scattering device making method which can make a surface enhanced Raman scattering device efficiently and stably.

BRIEF DESCRIPTION OF THE DRAWINGS

FIG. 5 is a perspective view illustrating steps of making the surface enhanced Raman scattering device of FIG. 1;

DESCRIPTION OF THE PREFERRED EMBODIMENTS

Figure 1:
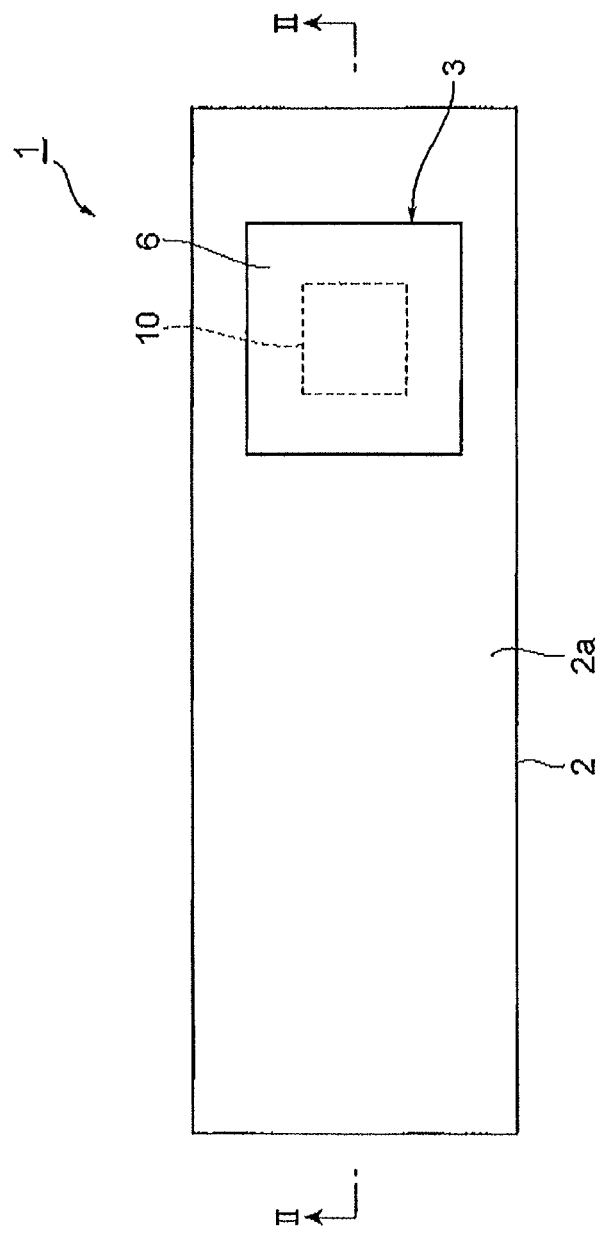
FIG. 1 is a plan view of a surface enhanced Raman scattering unit comprising the surface enhanced Raman scattering device in accordance with one embodiment.

In the following, embodiments will be explained in detail with reference to the drawings. In the drawings, the same or equivalent parts will be referred to with the same signs while omitting their overlapping explanations.

Figure 2:
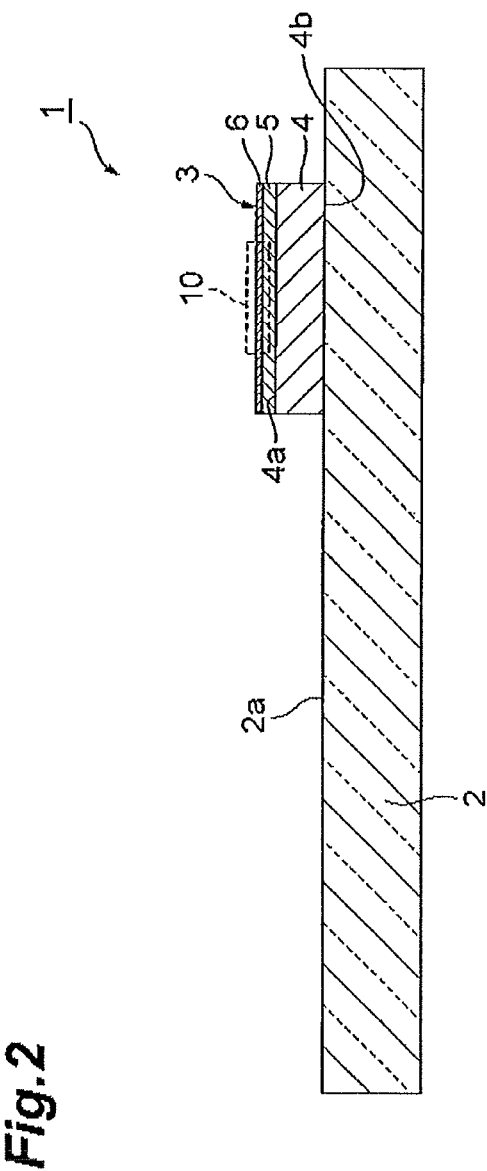
FIG. 2 is a sectional view taken along the line of FIG. 1.

As illustrated in FIGS. 1 and 2, a SERS unit (surface enhanced Raman scattering unit) 1 comprises a handling substrate 2 and a SERS device (surface enhanced Raman scattering device) 3 attached onto the handling substrate 2. The handling substrate 2 is a rectangular sheet-like glass slide, resin substrate, ceramic substrate, or the like. The SERS device 3 is arranged on a front face 2a of the handling substrate 2 while being lopsided to one longitudinal end part of the handling substrate 2.

The SERS device 3 comprises a substrate 4 attached onto the handling substrate 2, a formed layer 5 formed on the substrate 4, and a conductor layer 6 formed on the formed layer 5. The substrate 4 is formed from silicon, glass, or the like into a rectangular sheet having an outer shape on the order of several 100 μm×several 100 μm to several 10 mm×several 10 mm with a thickness on the order of 100 μm to 2 mm. The substrate 4 has a rear face 4b secured to the front face 2a of the handling substrate 2 by direct bonding, bonding with a metal such as solder, eutectic bonding, fusion bonding by irradiation with laser light or the like, anodic bonding, or bonding with a resin.

Figure 3:
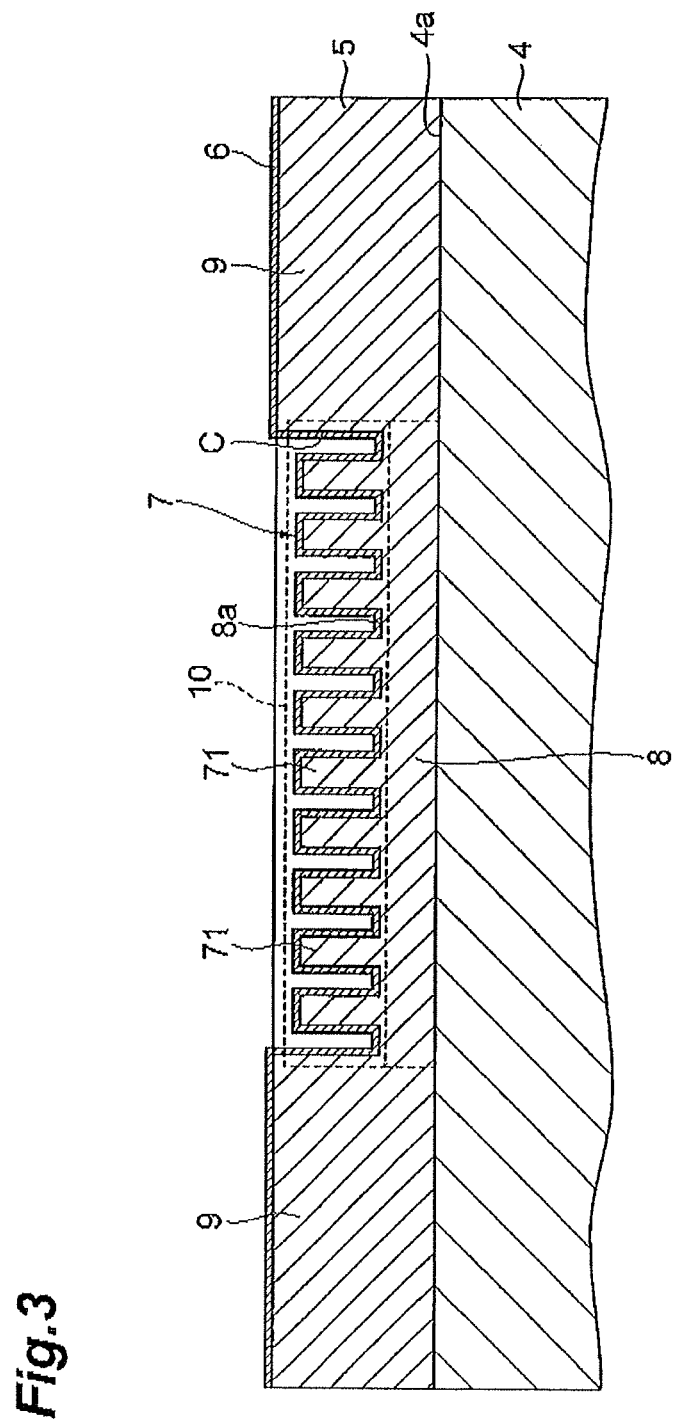
FIG. 3 is an enlarged sectional view of an optical function part in FIG. 2.

As illustrated in FIG. 3, the formed layer 5 includes a fine structural part 7, a support 8, and a frame 9. The fine structural part 7, which is a region having a periodic pattern, is formed on a surface on the side opposite from the substrate 4 at a center part of the formed layer 5. In the fine structural part 7, a plurality of cylindrical pillars 71 having a diameter and height in the order of several nm to several μm are periodically arranged with a pitch on the order of several 10 nm to several 100 nm along a front face (main surface) 4a of the substrate 4. The fine structural part 7 has a rectangular outer shape on the order of several 100 μm×several 100 μm to several 10 mm×several 10 mm when seen in the thickness direction of the substrate 4. The support 8, which is a rectangular region for supporting the fine structural part 7, is formed on the front face 4a of the substrate 4. The frame 9, which is a rectangular-ring-shaped region surrounding the fine structural part 7 and support 8, is formed on the front face 4a of the substrate 4. Each of the support 8 and frame 9 has a thickness on the order of several 10 nm to several 10 μm.

Figure 10:
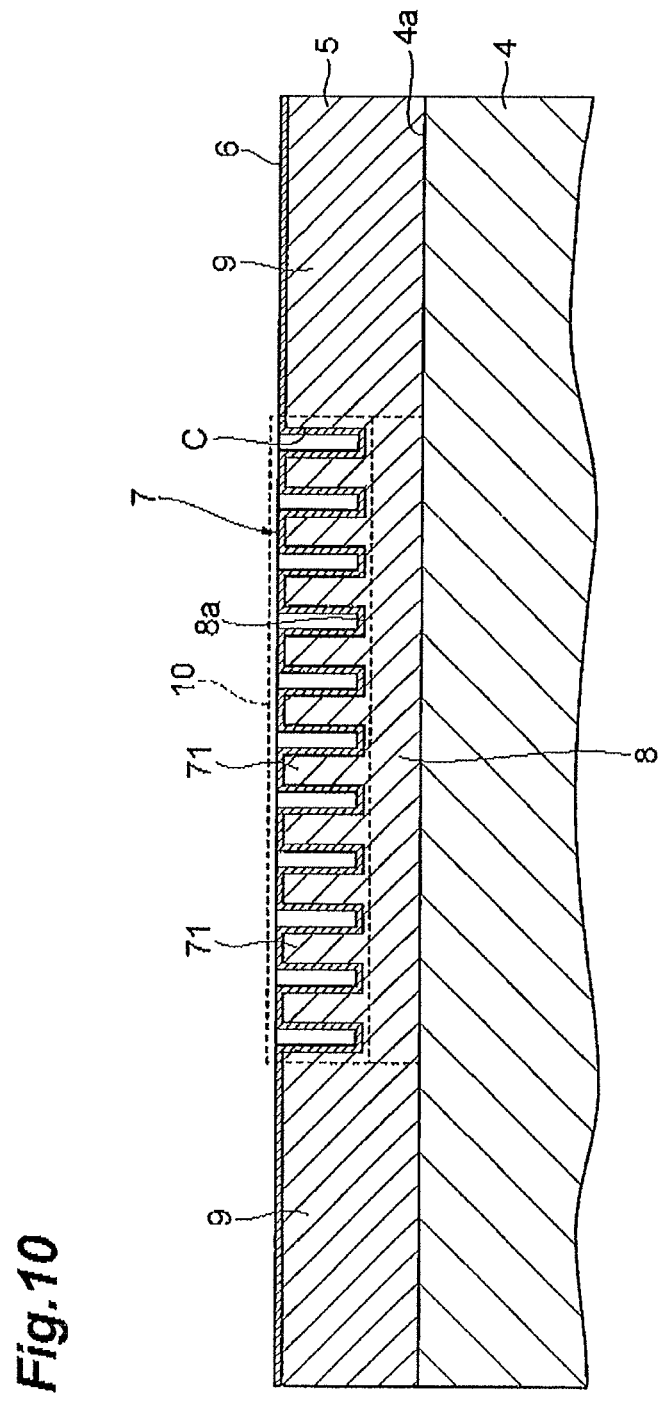
FIG. 10 is an enlarged sectional view illustrating a modified example of FIG. 3.

The distance from the front face 8a of the support 8 to the surface of frame 9 opposite from the substrate 4 (i.e., the height of the frame 9) is greater than the height of the fine structural part 7. The height of the frame 9 may also be substantially the same as that of the fine structural part 7 as illustrated in FIG. 10. The area of the contact surface between a replica mold R (which will be explained later) and the frame 9 at an end part of the fine structural part 7 is smaller (or, in other words, the surface energy becomes smaller) when the height of the frame 9 is substantially the same as that of the fine structural part 7 than when the height of the frame 9 is greater than that of the fine structural part 7. This makes it possible to inhibit both structures of the replica mold R and frame 9 at the end part of the fine structural part 7 from being damaged when releasing the replica mold R from the formed layer 5. The amount of the nanoimprint resin used in the formed layer 5 can also be made smaller. The height of the frame 9 may be made lower than that of the fine structural part 7, which also seems to yield the above-mentioned effects at the time of molding. From the viewpoint of protecting the fine structural part 7, however, it is desirable for the frame 9 to have a height not lower than that of the fine structural part 7. Hence, the above-mentioned effect at the time of forming and the protection of the fine structural part 7 can be satisfied at the same time when the frame 9 and fine structural part 7 have substantially the same height as illustrated in FIG. 10.

The formed layer 5 is integrally formed by molding a resin (examples of which include acrylic, epoxy, silicone, and urethane resins, PET, polycarbonates, and inorganic-organic hybrid materials) or low-melting glass arranged on the substrate 4 by nanoimprinting, for example.

The conductor layer 6 is formed so as to extend over the fine structural part 7 and frame 9. In the fine structural part 7, the conductor layer 6 is formed on the surfaces of the pillars 71 and the front face 8a of the support 8 exposed on the side opposite from the substrate 4. The conductor layer 6 has a thickness on the order of several nm to several µm. The conductor layer 6 is formed by vapor-depositing a conductor such as a metal (examples of which include Au, Ag, Al, Cu, and Pt) on the formed layer 5 molded by nanoimprinting, for example. In the SERS device 3, an optical function part 10 which generates surface enhanced Raman scattering is constructed by the conductor layer 6 formed on the surfaces of the pillars 71 and the surface 8a of the support 8.

Figure 4:
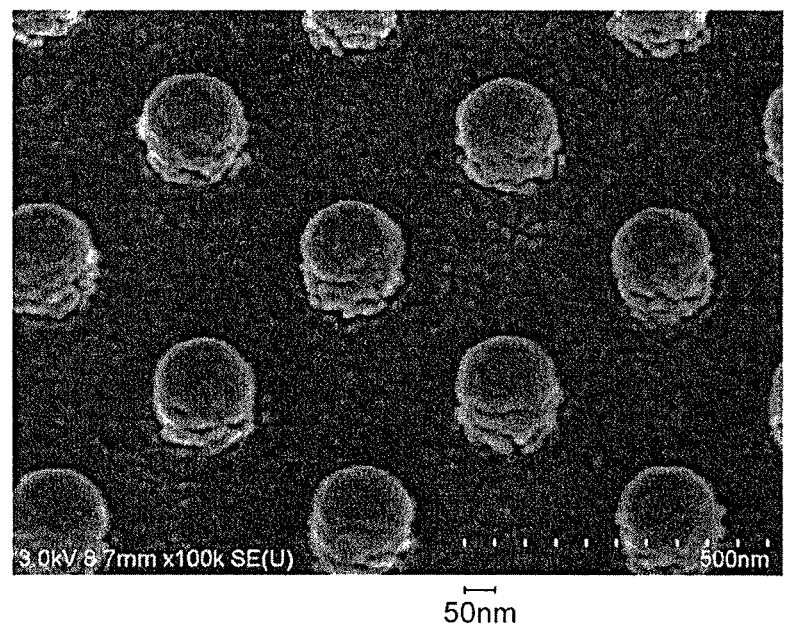
FIG. 4 is a SEM photograph of the optical function part in FIG. 2.

FIG. 4 is a SEM photograph of the optical function part in FIG. 2. The optical function part illustrated in FIG. 4 is one in which Au is vapor-deposited as a conductor layer with a thickness of 50 nm on a fine structural part made of a nanoimprint resin having a plurality of pillars (each having a diameter of 120 nm and a height of 180 nm) periodically arranged at a predetermined pitch (a distance of 360 nm between center lines).

Thus constructed SERS unit 1 is used as follows. First, the SERS unit 1 is prepared. Subsequently, using a pipette or the like, a solution sample (or a dispersion of a powder sample in a solution such as water or ethanol, as the case may be) is applied dropwise to a depression C defined by the support 8 and frame 9 of the formed layer 5, so that the sample is arranged on the optical function part 10. Subsequently, in order to reduce the lens effect, cover glass is mounted on the frame 9, and thereby come into close contact with the solution sample.

Next, the SERS unit 1 is set in a Raman spectrometer, and the sample arranged on the optical function part 10 is irradiated with excitation light through the cover glass. This generates surface enhanced Raman scattering at the interface between the optical function part 10 and the sample, whereby Raman scattered light derived from the sample is enhanced by about $10^8$ times, for example, and then emitted. Hence, highly sensitive and highly accurate Raman spectrometry is possible in the Raman spectrometer.

Not only the above-mentioned method, but the following methods may also be used for arranging the sample onto the optical function part 10. For example, the handling substrate 2 may be nipped so that the SERS device 3 is dipped into a solution sample (or a dispersion of a powder sample in a solution such as water or ethanol), lifted up therefrom, and then blown to dry. A minute amount of a solution sample (or a dispersion of a powder sample in a solution such as water or ethanol) may be applied dropwise onto the optical function part 10 and left to dry naturally. A powder sample may be dispersed as it is on the optical function part 10. Note that mounting of the cover glass is not indispensable at the time the measurement is conducted in these methods.

A method for making the SERS device 3 will now be explained. First, as illustrated in (a) of FIG. 5, a master mold M1 and a film base F are prepared. The master mold M1 has a plurality of patterns MP arranged in a matrix. Each pattern MP includes a fine structural part M7 corresponding to the fine structural part 7 and a support M8 supporting the fine structural part M7. In the master mold M1, the plurality of patterns MP are separated from each other by a frame M9 corresponding to the frame 9. Note that master mold M1 may be surface treated such as by applying mold lubricants or the like so as to enable easy demolding during a latter process.

Next, the film base F is pressed against the master mold M1 and pressurized and heated in this state, and thereby the patterns MP of the master mold M1 are transferred to the film base F (thermal nanoimprint). Subsequently, the film base F is released from the master mold M1, and thereby a replica mold (replica film) R having a plurality of patterns RP in the reverse of the patterns MP of the master mold M1 is yielded as illustrated in (b) of FIG. 5. In the replica mold R, the plurality of patterns RP are separated from each other. Here, the replica mold R is elastic and flexible. Its elasticity and flexibility derive from the material (examples of which include PET (polyethylene terephthalate), polycarbonate, silicone, polyimide, and fluorine resins) and thickness of the film base F, for example. This makes the replica mold R more elastic and flexible than molds formed from hard materials such as silica, silicon, and nickel. The replica mold R is also more elastic and flexible than a wafer 40 (which will be explained later). Repeating the foregoing process can yield a plurality of replica molds R. The replica mold R may also be formed by applying a resin (examples of which include epoxy, acrylic, fluorine, silicone, urethane, and inorganic-organic hybrid resins) onto the film base F. When the resin applied onto the film base is UV-curable, it may be cured by irradiation with UV instead of thermal nanoimprint, and thereby the replica mold R is yielded (UV nanoimprint). Note that replica mold R may be surface treated such as by applying mold lubricants or the like so as to enable easy demolding during a latter process.

Then, as illustrated in (c) of FIG. 5, the wafer 40 including a plurality of portions corresponding to the substrates 4 is prepared, and a UV-curable resin is applied to its front face 40a, and thereby a nanoimprint layer 50 to become the formed layer 5 is formed on the wafer 40.

Thereafter, the replica mold R is pressed against the nanoimprint layer 50 on the wafer 40, and the nanoimprint layer 50 is cured by irradiation with UV in this state, whereby a plurality of patterns RP in the replica mold R are transferred simultaneously to the nanoimprint layer 50. Subsequently, the replica mold R is released from the nanoimprint layer 50. This forms the formed layer 5 having fine structural parts 7 at respective portions corresponding to the substrates 4 on the wafer 40. A plurality of fine structural parts 7 are formed so as to be separated from each other by the frames 9, while the frames 9 adjacent to each other are formed so as to be continuous. Repeating the foregoing process can yield a plurality of wafers 40 each having the main surface 40a on which a plurality of fine structural parts 7 are formed.

Figure 6:
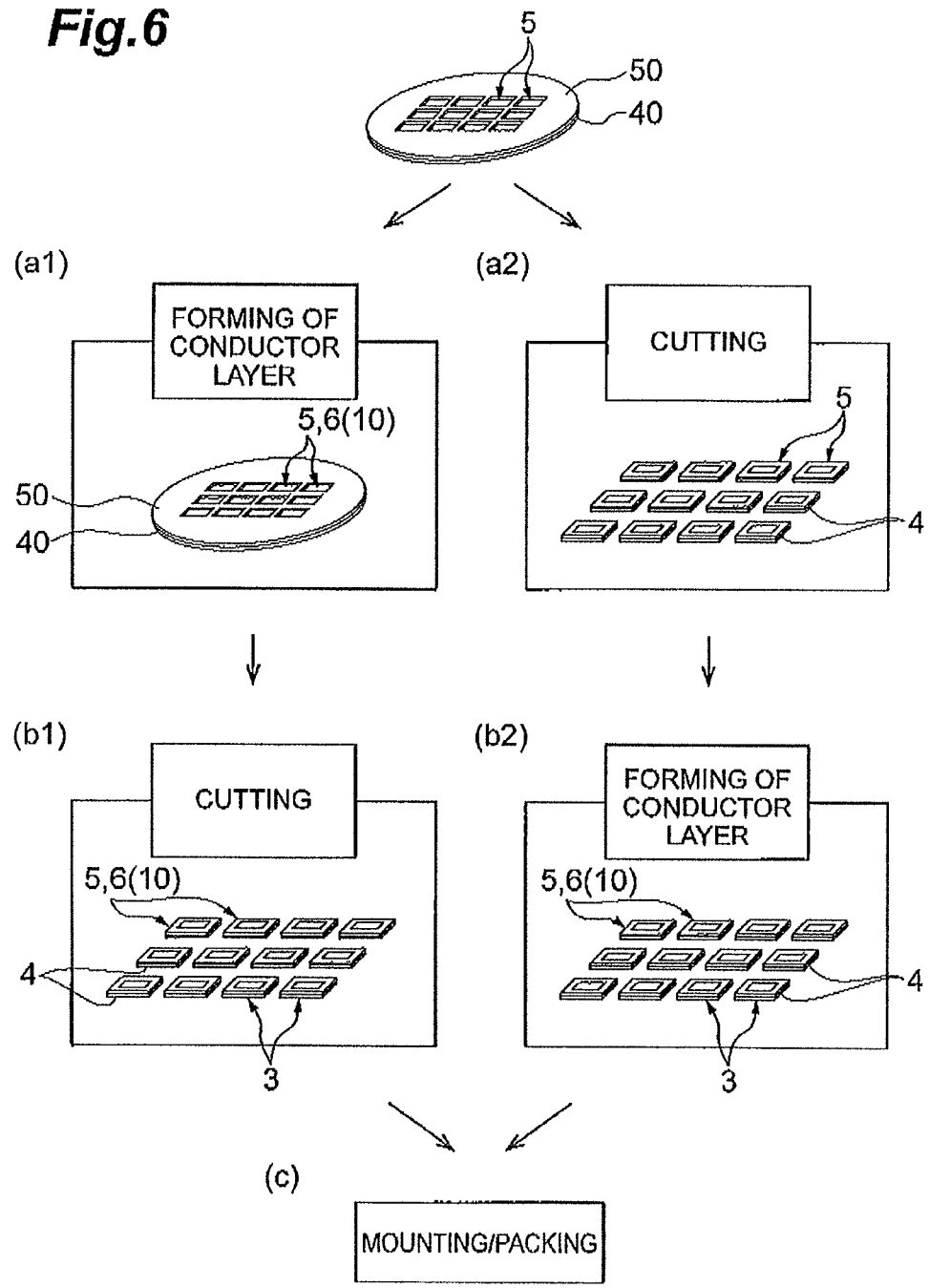
FIG. 6 is a perspective view illustrating steps of making the surface enhanced Raman scattering device of FIG. 1.

Next, as illustrated in (a1) of FIG. 6, a film of a metal such as Au or Ag is formed on the formed layer 5 by vapor deposition, such as resistance heating vapor deposition or electron beam vapor deposition, or sputtering, and thereby the conductor layer 6 is formed. This forms optical function parts 10 at respective portions corresponding to the substrates 4 on the wafer 40. On the wafer 40, the plurality of optical function parts 10 are formed so as to be separated from each other, while the conductor layer 6 is formed continuously over the frames 9 adjacent to each other. Subsequently, as illustrated in (b1) of FIG. 6, the wafer 40, formed layers 5, and conductor layer 6 are cut into the individual portions corresponding to the substrates 4, and thereby a plurality of SERS devices 3 are yielded. More specifically, lines to cut are set like grids so as to pass between the portions corresponding to the substrates 4, and the wafer 40 is cut along the lines, while the frames 9 of the formed layers 5 and conductor layer 6 existing on the lines are cut. Then, as illustrated in (c) of FIG. 6, the cut SERS device 3 is secured to (mounted on) the handling substrate 2, and thereby the SERS unit 1 is yielded, which is packed thereafter.

Here, the wafer 40 and formed layers 5 may be cut into chips for respective portions corresponding to the substrates 4 as illustrated in (a2) of FIG. 6, the conductor layer 6 may be formed on the fine structural part 7 of each chip as illustrated in (b2) of FIG. 6, and then mounting and packing may be performed as illustrated in (c) of FIG. 6. This can inhibit the conductor layer 6 including the optical function part 10 from being contaminated, since the conductor layer 6 is formed after cutting the wafer 40 and formed layers 5.

The above-mentioned cutting of the wafer 40 is performed as in the following, for example. The case of cutting the formed layers 5 and conductor layer 6 together with the wafer 40 (the case of (a1) and (b1) in FIG. 6) will be explained here.

Figure 7:
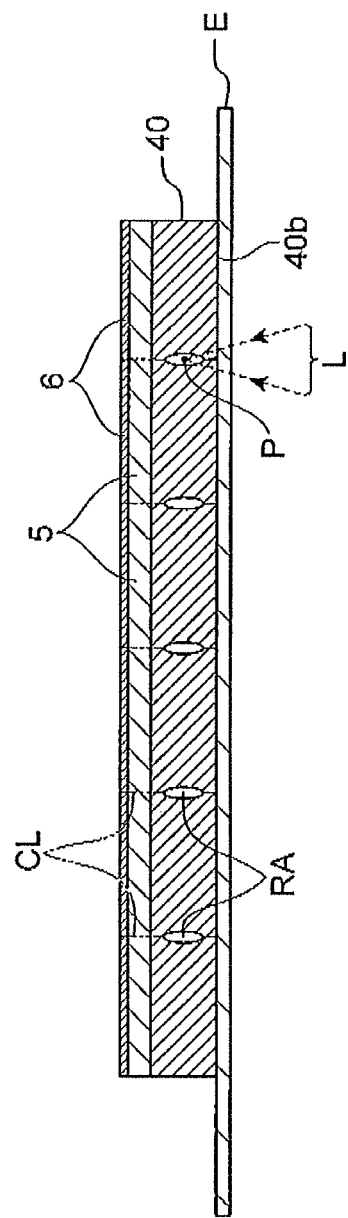
FIG. 7 is a sectional view illustrating a step of cutting a wafer.

First, as illustrated in FIG. 7, a tape E such as a light-transmitting expandable tape is attached to the rear face 40b of the wafer 40. Subsequently, the wafer 40 is irradiated with laser light L through the tape E while locating a converging point P within the wafer 40, and thereby modified regions RA are formed within the wafer 40 along lines to cut CL.

Figure 8:
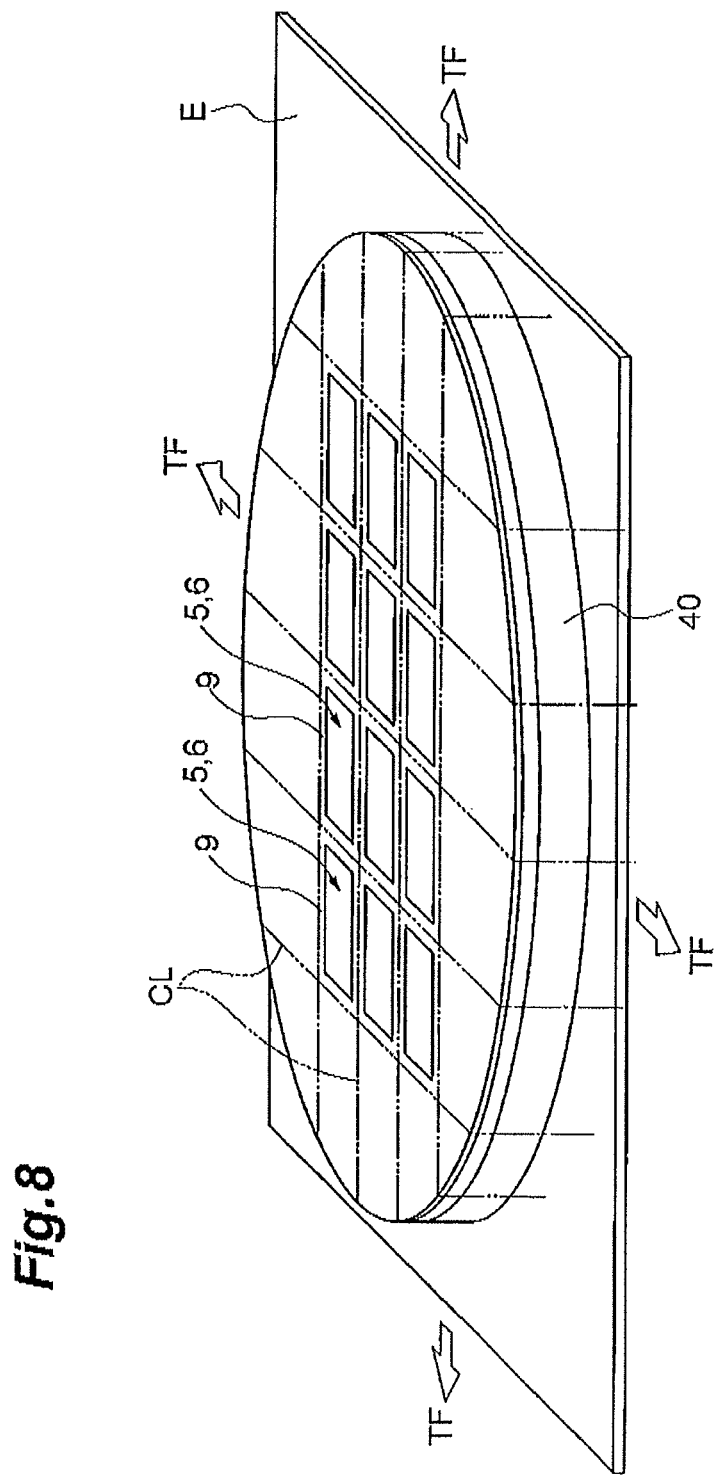
FIG. 8 is a perspective view illustrating a step of cutting the wafer.

Next, as illustrated in FIG. 8, a tensile load TF is applied to the tape E, so that fractures extend in the thickness direction of the wafer 40 from the modified regions RA, thereby cutting the frames 9 of the formed layers 5 and conductor layer 6 existing on the lines CL together with the wafer 40.

For cutting the frames 9 of the formed layers 5 and conductor layer 6 existing on the lines CL by utilizing the extension of fractures under the tensile load, it is preferred for the frame 9 and conductor layer 6 to have thicknesses of 50 μm or less and 2 μm or less, respectively. In this case, the frames 9 of the formed layers 5 and conductor layer 6 existing on the lines CL can be cut accurately along the lines CL.

As in the foregoing, the method for making the SERS device 3 transfers the patterns RP of the replica mold R to the nanoimprint layer 50 on the wafer 40, and thereby the formed layers 5 including the fine structural parts 7 are formed for the respective portions corresponding to the substrates 4. This can form the fine structural parts 7 efficiently and stably. Therefore, this method for making the SERS device 3 can make the SERS device 3 efficiently and stably.

In the above-mentioned method for making the SERS device 3, the step of cutting the wafer 40 into the respective portions corresponding to the substrates 4 is performed after the step of forming the conductor layer 6 on the fine structural parts 7. Therefore, the conductor layer 6 can be formed collectively for a plurality of fine structural parts 7 on the wafer 40, whereby the SERS device 3 can be made more efficiently.

In the above-mentioned method for making the SERS device 3, the replica mold R is flexible. This makes it easier to release the mold from the nanoimprint layer. The effect of making the mold easier to release is more favorably exhibited in the method of this embodiment, since the replica mold R having a plurality of patterns RP is used in order to form a plurality of formed layers 5 at the same time. When a hard mold is used, the mold and wafer 40 must be torn apart from each other in directions vertically opposite from each other, since the wafer 40, which is formed from silicon, glass, or the like, is also hard. In this case, the surface energy is so high that care must be taken for the peeling of the formed layers 5, damages to the mold and substrates 4, and the like. The flexible replica mold R, on the other hand, can be torn away from an end part with a small energy, which makes it easier to release, while inhibiting the formed layers 5 from peeling, the mold and substrates 4 from being damaged, and so forth.

In the above-mentioned method for making the SERS device 3, the replica mold R is flexible and thus follows relatively large distortions and the like, if any, of the wafer 40, whereby the fine structural parts 7 can be formed stably.

In the above-mentioned method for making the SERS device 3, the replica mold R is elastic. Here, when a hard mold is used, foreign matters and the like, if any, intervening between the replica mold R and the nanoimprint layer 50 may bite onto the nanoimprint layer 50, while a part of the nanoimprint layer 50 pushed back by the biting of the foreign matters may project so as to surround the foreign matters and the like. When a hard mold is used, a region to which the patterns RP are not transferred may occur in the nanoimprint layer 50 in the vicinity of the area where the foreign matters bite. When a hard mold is used, as the pressure is increased, foreign matters and the like may crush, thereby expanding defect regions such as those incurring projections and those having no patterns RP transferred thereto as mentioned above. When the elastic mold is used, on the other hand, foreign matters are likely to bite onto the mold, so that defect regions can be suppressed to a size on a par with that of the foreign matters and the like. This can suppress areas of transfer failures.

In the above-mentioned method for making the SERS device 3, the replica mold R is elastic, so that its patterns are easier to follow the nanoimprint layer 50. Hence, the fine structural parts 7 can be formed more stably.

In the above-mentioned method for making the SERS device 3, the replica mold R is elastic and thus follows relatively small roughness, if any, existing in the wafer 40, whereby the fine structural parts 7 can be formed more stably.

In the above-mentioned method for making the SERS device 3, the replica mold R has a plurality of patterns RP, and in the step of forming the formed layers 5 including the fine structural parts 7, the plurality of patterns RP are simultaneously transferred to the nanoimprint layer 50 by using the replica mold R. This makes it possible to form a plurality of fine structural parts 7 collectively for the nanoimprint layer 50 on the wafer 40, whereby the SERS device 3 can be made more efficiently.

When forming a plurality of formed layers 5 by so-called stepping and repeating, it is required to set a long distance between the patterns RP adjacent to each other in view of the case where the nanoimprint layer 50 protrudes out of its desirable area. In contrast, the above-mentioned method for making the SERS device 3 forms a plurality of formed layers 5 at the same time by using the replica mold R having a plurality of patterns RP and thus can arrange a greater number of patterns RP on the wafer 40 than when forming a plurality of formed layers 5 sequentially, whereby the SERS device 3 can be made more efficiently.

When forming the formed layers 5 by stepping and repeating, a plurality of formed layers 5 are formed sequentially for one wafer 40, which takes a very long time. Attention must also be paid to the fact that, during a plurality of molding operations, a part of the nanoimprint layer 50 may adhere to the replica mold R and transfer to the subsequently molded product, thereby lowering the yield. In contrast, the above-mentioned method for making the SERS device 3 forms a plurality of formed layers 5 at the same time and thus can attain high productivity and high yield.

In the above-mentioned method for making the SERS device 3, the plurality of patterns RP are separated from each other in the replica mold R, and in the step of forming the formed layers 5 including the fine structural parts 7, a plurality of patterns RP are simultaneously transferred to the nanoimprint layer 50 by using the replica mold R such that the plurality of fine structural parts 7 are separated from each other. Hence, the wafer 40 can be cut easily with reference to a space between the adjacent fine structural parts 7, 7 as a guide for cutting.

The above-mentioned method for making the SERS device 3 forms a plurality of fine structural parts 7 such that they are separated from each other. Hence, the method of this embodiment can vary the pitch of pillars 71 among a plurality of fine structural parts 7, for example.

When the pitch of the pillars 71 is set shorter in the case of forming the replica mold R by thermal nanoimprint or UV nanoimprint as mentioned above, the replica mold R is constructed relatively thin in its center part contributing to forming the fine structural parts 7 but relatively thick in its outer edge part. The SERS device 3 formed by this replica mold R is constructed relatively thick in its center part formed with the fine structural part 7 but relatively thin in its outer edge part. The SERS device 3 having the relatively thick center part is easier to keep the form of the fine structural part 7 at the center part when releasing the replica mold R from the formed layer 5. Hence, the SERS device 3 having the relatively thick center part has a characteristic of being able to inhibit the fine structural part 7 from being damaged.

When the pitch of the pillars 71 is set longer in the case of forming the replica mold R by thermal nanoimprint or UV nanoimprint, on the other hand, the replica mold R is constructed relatively thick in its center part contributing to forming the fine structural parts 7 but relatively thin in its outer edge part. The SERS device 3 formed by this replica mold R is constructed relatively thin in its center part formed with the fine structural part 7 but relatively thick in its outer edge part. The SERS device 3 having the relatively thin center part reduces the amount of deformation caused by shrinkage on curing or thermal expansion in the center part formed with the fine structural part 7. Furthermore, the SERS device 3 having the relatively thick outer edge part mitigates distortions caused by the difference in coefficient of thermal expansion with respect to the substrate 4. Hence, the SERS device 3 having the relatively thin center part has a characteristic of being able to stabilize the property of surface enhanced Raman scattering.

The above-mentioned method for making the SERS device 3 can vary the pitch of pillars 71 among a plurality of fine structural parts 7 and thus can simultaneously mold a plurality of SERS devices 3 having respective thickness distribution structures different from each other. Hence, the method of this embodiment can simultaneously form a plurality of SERS devices 3 for which respective characteristics different from each other are demanded.

In the above-mentioned method for making the SERS device 3, in the step of cutting the wafer 40 into the respective portions corresponding to the substrates 4, the formed layers 5 and conductor layer 6 existing on the lines CL passing between the portions corresponding to the substrates 4 are cut together with the wafer 40. This can integrally form the formed layers 5 and conductor layer 6 all over the portions corresponding to the substrates 4, whereby the SERS device 3 can be made more efficiently. Since the conductor layer 6 exists over the lines CL for cutting the wafer 40, the fine structural parts 7 can be arranged efficiently. This also makes it possible to omit the step for forming dicing lines in the formed layers 5 and conductor layer 6.

In the above-mentioned method for making the SERS device 3, in the step of cutting the wafer 40 into the respective portions corresponding to the substrates 4, fractures are extended from the modified regions R.A. formed in the wafer 40 along the lines CL, thereby cutting the formed layers 5 and conductor layer 6 existing on the lines CL together with the wafer 40. This makes it unnecessary to form the formed layers 5 and conductor layer 6 with cutting start points, whereby the fine structural parts 7 and optical function parts 10 can be inhibited from being damaged.

When cutting the formed layers 5 and conductor layer 6 by laser, for example, materials forming the formed layers 5 and conductor layer 6 may alter (e.g., change structures as being melted by heat and carbonize). When cutting the formed layers 5 and conductor layer 6 by blade dicing, for example, cutting blades, cutting agents (e.g., water, oils, and gases), and the like may contaminate the materials forming the formed layers 5 and conductor layer 6. In contrast, the above-mentioned method for making the SERS device 3 can prevent the materials of the formed layers 5 and conductor layer 6 from being altered, contaminated, and so forth.

In the above-mentioned method for making the SERS device 3, the formed layer 5 includes the support 8 for supporting the fine structural part 7 on the main surface 4*a* and the ring-shaped frame 9 for surrounding the support 8 on the main surface 4*a*, and in the step of cutting the wafer 40 into the respective portions corresponding to the substrate 4, fractures are extended from the modified regions RA formed in the wafer 40 along the lines CL passing between the portions corresponding to the substrates 4, thereby cutting the frames 9 and conductor layer 6 existing on the lines CL together with the wafer 40. Hence, the frames 9 can favorably buffer shocks caused by cutting and the like, whereby the fine structural part 7 and optical function part 10 can be inhibited from being damaged at the time of cutting.

In the above-mentioned method for making the SERS device 3, in the step of cutting the wafer 40 into the respective portions corresponding to the substrate 4, the wafer 40 is irradiated with the laser light L while locating the converging point P within the wafer 40, and thereby the modified regions RA are formed as cutting start points within the wafer 40 along the lines CL. Hence, the wafer 40 is hardly affected by the irradiation with the laser light L except for the vicinity of the converging point P of the laser light L therewithin, whereby the fine structural part 7 and optical function part 10 can be inhibited from being damaged at the time of cutting. Utilizing fractures having extended from the modified regions RA, the formed layers 5 and conductor layer 6 on the lines CL can accurately be cut together with the wafer 40.

When cutting the wafer 40 by blade dicing, for example, a protective film or the like for protecting the fine structural parts 7 is necessary. In contrast, the above-mentioned method for making the SERS device 3 can save the step of providing the protective film or the like. When providing the protective film or the like, care must be taken to keep the protective film from contaminating the fine structural parts 7. Such care is unnecessary in the above-mentioned method for making the SERS device 3.

When cutting the wafer 40 by blade dicing, for example, the formed layers 5 may peel from the substrate 4. In contrast, the above-mentioned method for making the SERS device 3 cuts the frames 9 and conductor layer 6 by a tensile load. Hence, the above-mentioned method for making the SERS device 3 can inhibit the formed layers 5 from peeling from the substrates 4.

Figure 9:
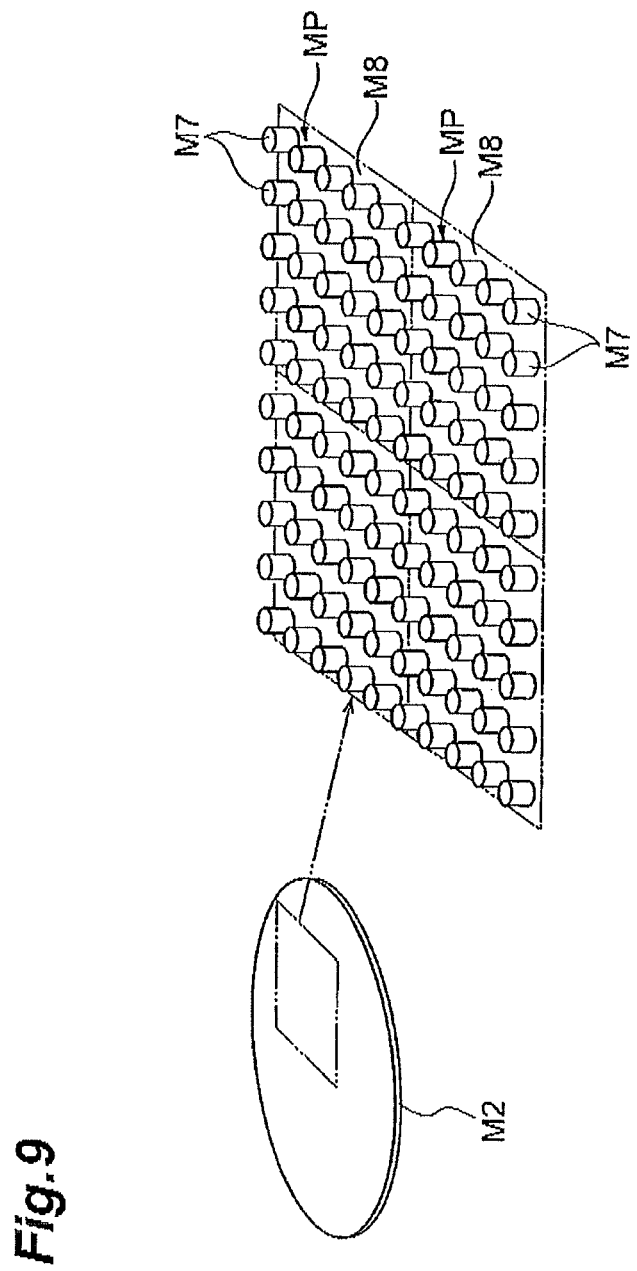
FIG. 9 is a perspective view illustrating a step of making the surface enhanced Raman scattering device in accordance with another embodiment.

A method for making a SERS unit in accordance with another embodiment will now be explained, FIG. 9 is a schematic view for explaining the method in accordance with another embodiment, This embodiment forms a plurality of fine structural parts 7 continuously in a nanoimprint layer 50 at the time of nanoimprinting.

In this embodiment, a pattern MP of a master mold M2 includes a fine structural part M7 corresponding to the fine structural part 7 of the formed layer 5 and a support M8 supporting the fine structural part M7. The master mold M2 does not include the frames M9 (see (a) of FIG. 5) corresponding to the frames 9 of the formed layers 5. In the master mold M2, a plurality of patterns MP are continuous.

The method of this embodiment using the master mold M2 transfers the patterns MP of the master mold M2 to a film base F by thermal nanoimprint or IN nanoimprint. Subsequently, the film base F is released from the master mold M2. This yields a replica mold R having a plurality of patterns RP in the reverse of the patterns MP of the master mold M2. In the replica mold R, the plurality of patterns RP are continuous.

Then, a wafer 40 including a plurality of portions corresponding to substrates 4 is prepared, and a nanoimprint resin is arranged over the plurality of portions corresponding to the substrates 4 on its front face (main surface) 40a, and thereby a nanoimprint layer 50 is formed integrally.

Next, the plurality of patterns RP in the replica mold R are transferred simultaneously to the nanoimprint layer 50 by nanoimprint. Here, a plurality of fine structural parts 7 are formed so as to be continuous. Performing the remaining steps as mentioned above can yield the SERS device 3 having pillars 71 formed close to outer edge parts of the formed layers 5.

As in the foregoing, in the method for making the SERS device 3, the patterns RP of the replica mold R are transferred to the nanoimprint layer 50 on the wafer 40, and thereby the formed layers 5 including the fine structural parts 7 are formed for the respective portions corresponding to the substrates 4. This can form the fine structural parts 7 efficiently and stably. Therefore, this method for making the SERS device 3 can make the SERS device 3 efficiently and stably.

In the above-mentioned method for making the SERS device 3, the step of cutting the wafer 40 into the respective portions corresponding to the substrates 4 is performed after the step of forming the conductor layer 6 on the fine structural parts 7. Therefore, the conductor layer 6 can be formed collectively for a plurality of fine structural parts 7 on the wafer 40, whereby the SERS device 3 can be made more efficiently.

In the above-mentioned method for making the SERS device 3, the replica mold R is flexible. This makes it easier to release the mold from the nanoimprint layer, while inhibiting the formed layers 5 from peeling, the mold and substrates 4 from being damaged, and so forth. In particular, the method of this embodiment uses the replica mold R having a plurality of patterns RP in order to form a plurality of formed layers 5 at the same time and thus more favorably exhibits the effects mentioned above.

In the above-mentioned method for making the SERS device 3, the replica mold R is flexible and thus follows relatively large distortions and the like, if any, of the wafer 40, whereby the fine structural parts 7 can be formed stably.

In the above-mentioned method for making the SERS device 3, the replica mold R is elastic. Therefore, foreign matters and the like, if any, intervening between the replica mold R and the nanoimprint layer 50 are likely to bite onto the mold R, so that defect regions can be suppressed to a size on a par with that of the foreign matters and the like. This can suppress areas of transfer failures.

In the above-mentioned method for making the SERS device 3, the replica mold R is elastic, so that its patterns are easier to follow the nanoimprint layer 50. Hence, the fine structural parts 7 can be formed more stably.

In the above-mentioned method for making the SERS device 3, the replica mold R is elastic and thus follows relatively small roughness, if any, existing in the wafer 40, whereby the fine structural parts 7 can be formed more stably.

In the above-mentioned method for making the SERS device 3, the replica mold R has a plurality of patterns RP, and in the step of forming the formed layers 5 including the fine structural parts 7, the plurality of patterns RP are simultaneously transferred to the nanoimprint layer 50 by using the replica mold R. This makes it possible to form a plurality of fine structural parts 7 collectively for the nanoimprint layer 50 on the wafer 40, whereby the SERS device 3 can be made more efficiently. This can also inhibit the nanoimprint layer 50 from protruding out as compared with the case of forming a plurality of formed layers 5 sequentially by so-called stepping and repeating, so that a greater number of patterns RP can be arranged on the wafer 40, whereby the SERS device 3 can be made more efficiently.

In the above-mentioned method for making the SERS device 3, a plurality of patterns RP are continuous in the replica mold R, and in the step of forming the formed layers 5 including the fine structural parts 7, a plurality of patterns are simultaneously transferred to the nanoimprint layer 50 by using the replica mold R such that the plurality of fine structural parts 7 are continuous. This can form a greater number of fine structural parts 7 in a small area than in the case where they are formed so as to be separated from each other.

In the above-mentioned method for making the SERS device 3, in the step of cutting the wafer 40 into the respective portions corresponding to the substrates 4, the formed layers 5 and conductor layer 6 existing on the lines CL passing between the portions corresponding to the substrates 4 are cut together with the wafer 40. This can integrally form the formed layers 5 and conductor layer 6 all over the portions corresponding to the substrates 4, whereby the SERS device 3 can be made more efficiently. Since the conductor layer 6 exists over the lines CL for cutting the wafer 40, the fine structural parts 7 can be arranged efficiently. This also makes it possible to save the step for forming dicing lines in the formed layers 5 and conductor layer 6.

In the above-mentioned method for making the SERS device 3, in the step of cutting the wafer 40 into the respective portions corresponding to the substrates 4, fractures are extended from the modified regions RA formed in the wafer 40 along the lines CL, thereby cutting the formed layers 5 and conductor layer 6 existing on the lines CL together with the wafer 40. This makes it unnecessary to form the formed layers 5 and conductor layer 6 with cutting start points, whereby the fine structural parts 7 and optical function parts 10 can be inhibited from being damaged. This can also prevent materials of the formed layers 5 and conductor layer 6 from being altered, contaminated, and so forth.

In the above-mentioned method for making the SERS device 3, in the step of cutting the wafer 40 into the respective portions corresponding to the substrate 4, the wafer 40 is irradiated with the laser light L while locating the converging point P within the wafer 40, and thereby the modified regions RA are formed as cutting start points within the wafer 40 along the lines CL. Hence, the wafer 40 is hardly affected by the irradiation with the laser light L except for the vicinity of the converging point P of the laser light L therewithin, whereby the fine structural part 7 and optical function part 10 can be inhibited from being damaged at the time of cutting. Utilizing fractures having extended from the modified regions RA, the formed layers 5 and conductor layer 6 on the lines CL can accurately be cut together with the wafer 40. This can save the step of providing a protective film or the like and prevent the protective film or the like from contaminating the fine structural parts 7. This can also inhibit the formed layers 5 from peeling from the substrates 4.

The present invention is not limited to the embodiments explained in the foregoing. For example, the cross-sectional forms of the pillars 71 are not necessarily circular, but may also be elliptical or polygonal, e.g., triangular or quadrangular. Thus, various materials and forms can be employed for each structure of the SERS device 3 without being restricted to those mentioned above. Furthermore, the arrangement of the pillars 71 is not limited to a matrix, but it may be a staggered arrangement, a triangular grid arrangement, a random arrangement, or the like.

The conductor layer 6 may be formed on the fine structural parts 7 either directly or indirectly through any layers such as layers of buffer metals (e.g., Ti and Cr) for improving the adhesion of metals to the fine structural parts 7.

The frame 9 may surround the support 8 alone instead of the support 8 and fine structural part 7.

In the nanoimprint step illustrated in (a) to (c) of FIG. 5, a plurality of formed layers may be formed sequentially by repeatedly using a replica mold having a size smaller than that of the wafer 40 (stepping and repeating) as mentioned above.

Figure 11:
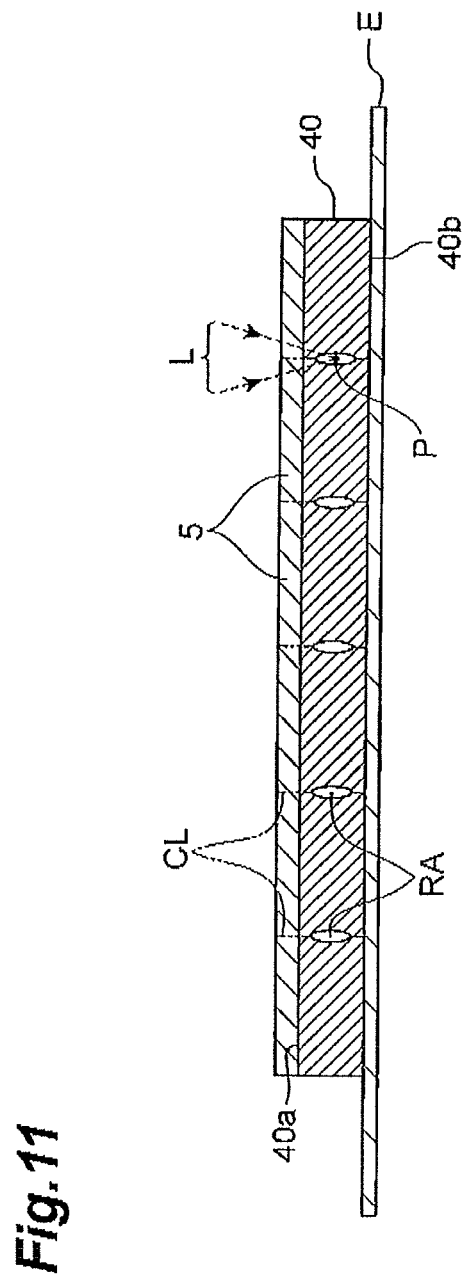
FIG. 11 is a sectional view illustrating a modified example of the step of cutting the wafer.
Figure 12:
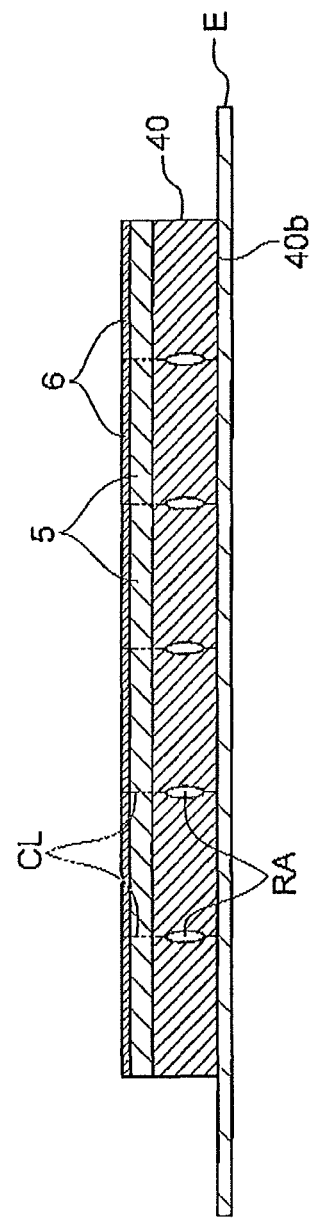
FIG. 12 is a sectional view illustrating the modified example of the step of cutting the wafer.
Figure 13:
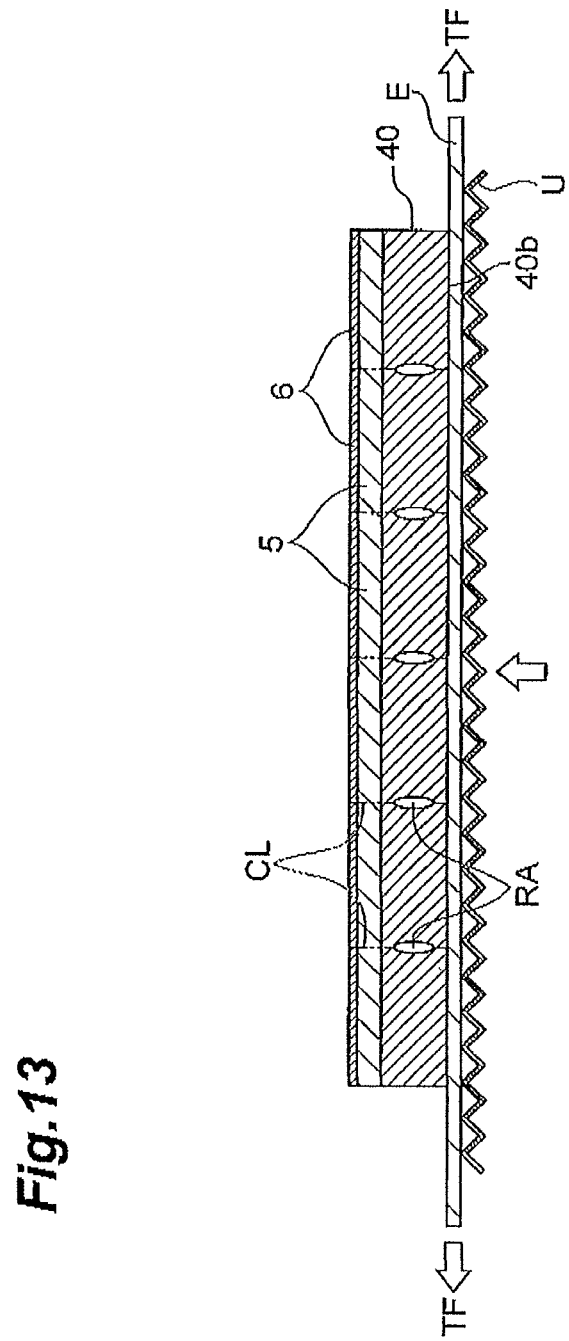
FIG. 13 is a sectional view illustrating the modified example of the step of cutting the wafer.

When cutting the wafer 40 by extending fractures from the modified regions RA, the modified regions RA may be formed before making the conductor layer 6. FIGS. 11 to 13 are sectional views illustrating a modified example of the step of cutting the wafer.

First, as illustrated in FIG. 11, the tape E is attached to the rear face 40b of the wafer 40 before making the conductor layer 6 after forming the formed layers 5. Subsequently, the wafer 40 is irradiated with the laser light L through the formed layers 5 from the front face 40a side while locating the converging point P within the wafer 40, and thereby the modified regions RA is formed within the wafer 40 along the lines CL. In this example, the tape E is not required to be transparent to light. The tape E may be attached to the rear face 40b of the wafer 40 after forming the conductor layer 6, which will be explained later. The type of the tape E may be changed according to the stage of forming the modified regions RA in FIG. 11 and respective stages of forming the conductor layer 6 in FIG. 12 and cutting the wafer 40 in FIG. 13, which will be explained later.

Next, as illustrated in FIG. 12, a film of a metal such as Au or Ag is formed on the formed layers 5, and thereby the conductor layer 6 is made. This forms the optical function parts 10 at respective portions corresponding to the substrates 4 on the wafer 40.

Subsequently, while the tensile load TF is applied to the tape E, a cutting assisting unit U having irregularities (e.g., saw-like irregularities) is struck on the rear face 40b of the wafer 40 through the tape E, so as to extend fractures in the thickness direction of the wafer 40 from the modified regions RA formed within the wafer 40, thereby cutting the frames 9 of formed layers 5 and conductor layer 6 existing on the lines CL together with the wafer 40. This yields a plurality of SERS devices 3. Then, thus cut SERS device 3 is secured (mounted) to the handling substrate 2, and thereby the SERS unit 1 is yielded, which is packed thereafter.

In this example, the wafer 40 is irradiated with the laser light L from the front face 40a side, which makes it unnecessary for the tape E to be transparent to light. This can widen the range of selectable types of the tape B.

The step of cutting the wafer 40 into the respective portions corresponding to the substrates 40 is performed after the step of forming the conductor layer 6 on the fine structural parts 7, so that the conductor layer 6 can be formed collectively for a plurality of fine structural parts 7 on the wafer 40, whereby the SERS device 3 can be manufactured more efficiently.

The modified regions RA are formed before making the conductor layer 6; after forming the conductor layer 6, the wafer 40 is cut by extending fractures from the modified regions RA, and then mounted and packed, whereby the time elapsing before mounting and packing after forming the conductor layer 6 can be made shorter, and thereby the conductor layer 6 including the optical function parts 10 is inhibited from being contaminated.

REFERENCE SIGNS LIST

3 . . . SERS device (surface enhanced Raman scattering device); 4 . . . substrate; 4a. . . front face (main surface); 5 . . . formed layer; 6 . . . conductor layer; 7 . . . fine structural part; 8 . . . support; 9 . . . frame; 10 . . . optical function part;

40 . . . wafer; 40a . . . front face (main surface); 50 . . . nanoimprint layer; R . . . replica mold; RA . . . modified region; RP . . . pattern

What is claimed is:

1. A method for making a surface enhanced Raman scattering unit comprising a substrate; a fine structural part provided to the substrate; and a conductor layer formed on the fine structural part and constituting an optical function part for generating surface enhanced Raman scattering; the method comprising:
    a first step of providing a wafer including a plurality of portions each corresponding to the substrate;
    a second step of providing the fine structural part to the wafer for each portion corresponding to the substrate by transferring a pattern corresponding to the fine structural part after the first step;
    a third step of forming the conductor layer on the fine structural part after the second step; and
    a fourth step of cutting the wafer into each portion corresponding to the substrate after the second step.

2. The method for making a surface enhanced Raman scattering unit according to claim 1, wherein, in the second step, a nanoimprint layer is formed on a main surface of the wafer, and the pattern is transferred to the nanoimprint layer by using a mold having the pattern corresponding to the fine structural part.

3. The method for making a surface enhanced Raman scattering unit according to claim 2, wherein the mold has a plurality of such patterns; and
    wherein, in the second step, a plurality of the patterns are simultaneously transferred to the nanoimprint layer by using the mold.

4. The method for making a surface enhanced Raman scattering unit according to claim 1, wherein, in the third step, the conductor layer is simultaneously formed on the fine structural part of the plurality of portions each corresponding to the substrate.

5. The method for making a surface enhanced Raman scattering unit according to claim 1, wherein, in the third step, the conductor layers is formed continuously over a main surface of the wafer.

* * * * *